(12) United States Patent
McGhee

(10) Patent No.: US 7,998,462 B2
(45) Date of Patent: Aug. 16, 2011

(54) LINKERS FOR ANCHORING TARGETING LIGANDS

(75) Inventor: William D. McGhee, Fenton, MO (US)

(73) Assignee: Kereos, Inc., St. Louis, MO (US)

( * ) Notice: Subject to any disclaimer, the term of this patent is extended or adjusted under 35 U.S.C. 154(b) by 916 days.

(21) Appl. No.: 11/872,984

(22) Filed: Oct. 16, 2007

(65) Prior Publication Data
US 2008/0305037 A1  Dec. 11, 2008

Related U.S. Application Data

(60) Provisional application No. 60/853,824, filed on Oct. 24, 2006.

(51) Int. Cl.
*A61B 5/055* (2006.01)
*A61K 51/00* (2006.01)
*A61M 36/14* (2006.01)
*A61K 31/00* (2006.01)

(52) U.S. Cl. .............. 424/9.321; 424/1.11; 424/1.21; 424/1.65; 424/9.36; 424/812; 514/709

(58) Field of Classification Search .............. 424/1.21, 424/9.321, 9.51, 1.11, 1.65, 9.36, 812; 977/907; 514/709
See application file for complete search history.

(56) References Cited

U.S. PATENT DOCUMENTS

| 6,332,770 | B1 | 12/2001 | Oueslati et al. | |
|---|---|---|---|---|
| 6,511,649 | B1 | 1/2003 | Harris et al. | |
| 2004/0013720 | A1* | 1/2004 | Ellens et al. | 424/450 |
| 2009/0317475 | A1* | 12/2009 | Beardsley et al. | 424/489 |

FOREIGN PATENT DOCUMENTS

WO  WO-03/062198  7/2003

OTHER PUBLICATIONS

International Search Report for PCT/US07/81540, mailed on Aug. 5, 2008, 3 pages.
Written Opinion of the International Searching Authority for PCT/US07/81540, mailed on Aug. 5, 2008, 6 pages.

* cited by examiner

*Primary Examiner* — Michael G Hartley
*Assistant Examiner* — Leah Schlientz
(74) *Attorney, Agent, or Firm* — Morrison & Foerster LLP

(57) ABSTRACT

An improved linker which lacks chiral centers between a hydrophobic anchor for coupling to lipid-based particles and a targeting agent has suitable hydrophobic/hydrophilic properties for use in vivo.

12 Claims, No Drawings

LINKERS FOR ANCHORING TARGETING LIGANDS

CROSS-REFERENCE TO RELATED APPLICATION

This application claims benefit of U.S. provisional application Ser. No. 60/853,824 filed 24 Oct. 2006, the contents of which are incorporated by reference herein.

TECHNICAL FIELD

The invention is directed to compositions and methods for anchoring targeting agents to lipid/surfactant based compositions. In one embodiment, fluorocarbon nanoparticles coated with lipid/surfactant layers are targeted to desired in vivo destinations using targeting agents by embedding the compounds of the invention in the lipid/surfactant coating.

BACKGROUND ART

PCT Publication WO 2003/062198 describes integrin targeted nanoparticles as imaging agents and drug carriers wherein the targeting moiety is coupled to the particle through anchoring a linker coupled to a peptidomimetic into a lipid/surfactant layer coating the particles. Exemplified as such a linker is a long chain polyamide containing two chiral centers and including a segment of polyethylene glycol (PEG). The linker is coupled to phosphatidyl ethanolamine (PE) through an amide linkage to the nitrogen of the ethanolamine.

The present invention is directed to improved linkers which couple targeting agents to lipid/surfactant anchoring moieties.

DISCLOSURE OF THE INVENTION

The invention is directed to improvements in linking moieties that can couple targeting agents to anchoring components. The improved linkers contain hydrophilic regions represented by polyethylene glycol (PEG) and an extension lacking chiral centers that is coupled to a targeting agent.

Thus, in one aspect, the invention is directed to compounds of the formula.

targeting agent-SO$_2$-phenylene-O(CH$_2$)$_n$CONH (CH$_2$)$_n$ NHCO(CH$_2$)$_n$—CONH(CH$_2$)$_n$O (CH$_2$CH$_2$O)$_x$ CH$_2$CH$_2$OCZ-anchor     (1)

wherein each n is independently 1-4;
x is an integer of 20-60;
Z is =NH or =O;
the phenylene may optionally be substituted by alkyl, alkenyl or alkynyl;
the targeting agent is a moiety containing an amino group or a hydroxyl group for coupling to the remainder of the molecule; and
the anchor is a lipophilic compound for embedding the compound in a lipid/surfactant based particulate composition, which anchor also contains an amino group or a hydroxyl group for coupling to the remainder of the molecule.

In other aspects, the invention is directed to targeted lipid/surfactant based particles that comprise the compound of formula (1) and to methods to deliver such particles comprising the compound of formula (1) to a destination in vivo by administering to a subject a composition containing particles comprising the compound of formula (1). The targeted particles may further comprise therapeutic agents and/or contrast agents or other moieties for imaging. The particles may further contain radioisotopes for diagnosis or treatment of conditions associated with the targeted destination in vivo.

MODES OF CARRYING OUT THE INVENTION

The invention provides improved linkers shown included the structure of the compound of formula (1) that couple a targeting agent to an anchor. The linkers have characteristics that make them suitable for in vivo administration and lack chiral centers so as to provide more efficient synthesis and delivery. The phenylene sulfonyl residue in the linker (which is preferably the para isomer) results from the use of a coupling agent that readily reacts with an amino or hydroxyl group contained in the targeting agent and the —OCZ— group results from coupling of the linker to an amino or hydroxyl group contained in the anchor. One convenient anchor is a phosphatidyl ethanolamine (PE), or a monoacyl or diacyl glycerol, with two acyl residues of suitable length to provide a proper lipophilicity. Typical chain lengths range from 12-22 carbon atoms and the chains may be saturated or unsaturated. Analogs of phosphatidyl ethanolamine (PE) such as phosphatidyl glycerol, phosphatidyl inositol could also be used, but as phosphatidyl ethanolamine (PE) is a common natural product, this offers considerable convenience. Other possibilities include cholesterol and cholesterol esters or other lipid-compatible substances that contain hydroxyl or amino groups for coupling to the remainder of the linker.

The targeting agents may be antibodies or portions thereof, or may be aptamers, peptidomimetics, receptor ligands and the like. "Antibodies" includes immunoreactive fragments and derivatives, such as single chain antibodies and F$_v$ fragments. Particularly useful in some aspects of the invention are targeting agents that target integrins, such as α$_v$β$_3$. These may be peptides containing an RGD sequence, or may include the mimetics set forth, for example, in U.S. Pat. Nos. 6,153,628; 6,130,231; or 6,322,770, all incorporated by reference for their disclosure of suitable mimetics.

As noted above, the phenylene moiety shown in formula (1) is preferably a para isomer of the sulfono group and the hydroxyl coupled to the remainder of the chain. The phenylene moiety may be substituted by one or more alkyl, alkylene, or alkynylene groups. Typically, the alkyl groups contain 1-8C, or alternatively 1-4C and the number of carbons in the unsaturated forms is a minimum, of course, of two. These groups include straight chain and branched chain and cyclic forms and combinations of these. Typical groups are methyl, ethyl, isobutyl, cyclohexylmethyl, cyclopentylmethyl and the like. Preferred are shorter substituents, such as methyl, ethyl or propyl or the corresponding unsaturated forms of methyl or propyl.

The indicated polyethylene glycol residue contains 20-60 monomers, preferably 40-50 monomers. Thus, x may be 20, 30, 40, 50 or 60 or the integers intervening.

The compounds of formula (1) are typically prepared by coupling the targeting agent to a sulfonyl chloride derivative of benzene which has been coupled to at least a portion of the remainder of the linker at the terminus that will be distal from the anchor. The linker itself can be formed by reacting the intermediate portions with a derivatized polyethylene glycol derivative of the anchor. A detailed exemplary description is provided below.

A particularly preferred compound of the invention is the compound of formula (2):

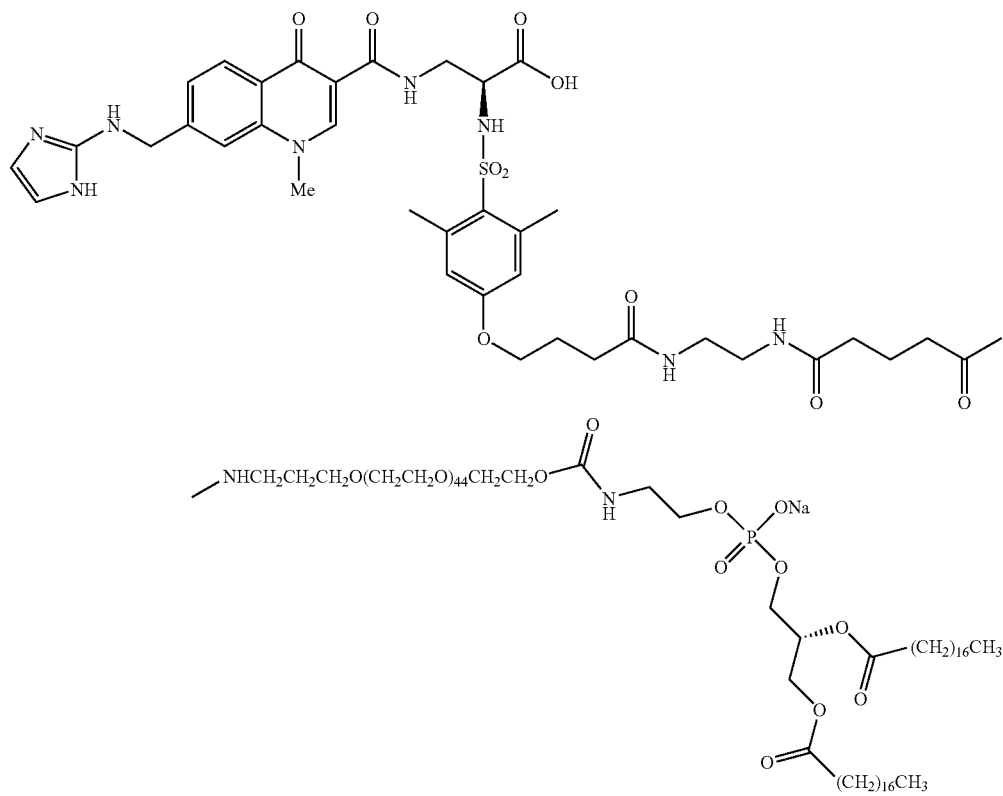

As noted above, the compounds of the invention are coupled by virtue of the anchoring moiety to lipid-based particulate carriers. In one embodiment, the anchor is embedded in the lipid surfactant layer of a suitable nanoparticle compound of fluorocarbon or oil or both. In addition to liquid fluorocarbon lipid/surfactant-coated nanoparticles, lipid-based particulate carriers that will accommodate the anchor include liposomes, micelles, and oil-based emulsions. The nature of these embodiments is well known in the art.

Thus, particulate lipid-based vehicles may include liposomes, lipid micelles, lipoprotein micelles, lipid-stabilized emulsions, fluorocarbon/oil nanoparticles and the like. Liposomes can be prepared as described in *Liposomes: Rational Design* (A. S. Janoff, ed., Marcel Dekker, Inc., N.Y.), or by additional techniques known to those knowledgeable in the art. Some liposomes are "cholesterol deficient". The term "cholesterol deficient" as used herein with reference to a liposome means that a liposome is prepared with the absence of cholesterol with an amount of cholesterol that is insufficient to significantly alter the phase transition characteristics of the liposome (typically less than 20 mol % cholesterol). Liposomes may also contain therapeutic lipids, which include ether lipids, phosphatidic acid, phosphonates, ceramide and ceramide analogues, sphingosine and sphingosine analogues and serine-containing lipids. Liposomes may also be prepared with surface stabilizing hydrophilic polymer-lipid conjugates such as polyethylene glycol-DSPE, to enhance circulation longevity. Negatively charged lipids such as phosphatidylglycerol (PG) and phosphatidylinositol (PI) may also be added to liposome formulations to increase the circulation longevity of the carrier. These lipids may be employed to replace hydrophilic polymer-lipid conjugates or cholesterol as surface stabilizing agents. Embodiments of this invention may make use of cholesterol-deficient liposomes containing PG or PI to prevent aggregation thereby increasing the blood residence time of the carrier.

Micelles are self-assembling particles composed of amphipathic lipids or polymeric components that are utilized for the delivery of sparingly soluble agents present in the hydrophobic core. Various means for the preparation of micellar delivery vehicles are available and may be carried out with ease by one skilled in the art. For instance, lipid micelles may be prepared as described in Perkins, et al., *Int. J. Pharm.* (2000) 200(1):27-39. Lipoprotein micelles can be prepared from natural or artificial lipoproteins including low and high-density lipoproteins and chylomicrons. Lipid-stabilized emulsions are micelles prepared such that they comprise an oil filled core stabilized by an emulsifying component such as a monolayer or bilayer of lipids. The core may comprise fatty acid esters such as triacylglycerol (corn oil). The monolayer or bilayer may comprise a hydrophilic polymer lipid conjugate such as DSPE-PEG. These delivery vehicles may be prepared by homogenization of the oil in the presence of the polymer lipid conjugate. Agents that are incorporated into lipid-stabilized emulsions are generally poorly water-soluble. Synthetic polymer analogues that display properties similar to lipoproteins such as micelles of stearic acid esters or poly(ethylene oxide) block-poly(hydroxyethyl-L-aspartamide) and poly(ethylene oxide)-block-poly(hydroxyhexyl-L-aspartamide) may also be used in the practice of this invention (Lavasanifar, et al., *J. Biomed. Mater. Res.* (2000) 52:831-835).

Techniques for preparing suitable nanoparticles useful in the present invention which contain fluorocarbon cores coated with a lipid/surfactant are described in U.S. Pat. Nos. 7,186,399 and 6,676,963, incorporated herein by reference.

In a typical procedure for preparing the emulsions of one exemplary embodiment, a fluorochemical liquid and the components of the lipid/surfactant coating are fluidized in aqueous medium to form an emulsion. The functional components of the surface layer may be included in the original emulsion, or may later be covalently coupled to the surface layer subsequent to the formation of the nanoparticle emulsion. The number of targeting agents provided by the compounds of formula (1) per particle is typically the order of several hundred.

When appropriately prepared, the lipid-based particles may comprise ancillary agents. These ancillary agents may be therapeutic agents, radionuclides, chelates for providing contrast agents for MRI, or other materials to be carried to the target. Generally, if an ancillary agent is present, the particles contain a multiplicity of such agents at their outer surface or otherwise contained within the particle. In such cases, the lipid-based particles typically contain hundreds or thousands of molecules of a biologically active agent, radionuclide and/or MRI contrast agent. For MRI contrast agents, the number of copies of a component to be coupled to the lipid-based particle is typically in excess of 5,000 copies per particle, more preferably 10,000 copies per particle, still more preferably 30,000, and still more preferably 50,000-100,000 or more copies per particle. The number of copies of fluorophores, radionuclides, and biologically active agents is variable.

The lipid-based particles need not contain an ancillary agent. In general, the targeted particles, directly coupled to a targeting ligand, are useful themselves as ultrasound contrast agents. Further, if the particles have a fluorocarbon core, $^{19}F$ magnetic resonance imaging can be used to track the location of the particles concomitantly with their additional functions described above. However, the inclusion of other components in multiple copies renders them useful in other respects. For instance, the inclusion of a chelating agent containing a paramagnetic ion makes the emulsion useful as a magnetic resonance imaging contrast agent. The inclusion of biologically active materials makes them useful as drug delivery systems. The inclusion of radionuclides makes them useful either as therapeutic for radiation treatment or as diagnostics for imaging. Other imaging agents include fluorophores, such as fluorescein or dansyl. Biologically active agents may also be included when the particulate carriers comprise imaging agents. A multiplicity of such activities may be included; thus, images can be obtained of targeted tissues at the same time active substances are delivered to them.

Emulsions containing particulate carriers with lipid/surfactant layers can be prepared in a range of methods depending on their nature. In one procedure, used for illustrative purposes only, the following procedure is set forth for an emulsion containing a drug: A surfactant co-mixture (2.0% w/v) and glycerin (1.7% w/v) is prepared where the surfactant co-mixture includes 64 mole % lecithin (Pharmacia Inc), 35 mole % cholesterol (Sigma Chemical Co.) and 1 mole % of the compound of formula (1) dissolved in chloroform. A drug is suspended in methanol (~25 μg/20 μl) and added in titrated amounts between 0.01 and 5.0 mole % of the 2% surfactant layer, preferably between 0.2 and 2.0 mole %. The chloroform-lipid mixture is evaporated under reduced pressure, dried in a 50° C. vacuum oven overnight and dispersed into water by sonication. The suspension is transferred into a blender cup (Dynamics Corporation of America) with perfluorooctylbromide (PFOB) in distilled or deionized water and emulsified for 30 to 60 seconds. The emulsified mixture is transferred to a Microfluidics emulsifier (Microfluidics Co.) and continuously processed at 20,000 PSI for three minutes. The completed emulsion is vialed, blanketed with nitrogen and sealed with stopper crimp seal until use. A control emulsion can be prepared identically excluding the drug from the surfactant commixture. Particle sizes are determined in triplicate at 37° C. with a laser light scattering submicron particle size analyzer (Malvern Zetasizer 4, Malvern Instruments Ltd., Southborough, Mass.), which indicate tight and highly reproducible size distribution with average diameters less than 400 nm. Unincorporated drug can be removed by dialysis or ultrafiltration techniques.

Alternatively, the emulsions may be prepared by the following illustrative procedure where an ancillary agent which is a chelate for MRI is included:

Buffered water (WFI) is prepared by the addition of EDTA salt (USP) suitable for desired pH range and of sufficient buffering capacity to maintain pH throughout shelf life of emulsion followed by the addition of glycerin. The buffered water is added to a mixing tank followed by the addition of the compound of formula (1), Gd-Amide Chelate and PFOB and the surfactant mixture described above.

The mixture is circulated through a high sheer mixer at ambient temperature and then continuously circulated through a Microfluidizer (Microfluidics) with tanks manufactured by Mueller validated for cGMP manufacture and maintained at an operating pressure of 15,000 psi. The temperature of the process stream is controlled by a heated/refrigerated circulator connected to a process fluid heat exchanger. Temperature is monitored in line.

The pH of the resulting emulsion is measured prior to vial filling. Clear serum vials are filled to a controlled volume (by weight) with the headspace swept with inert gas and then stoppered and capped.

Terminal Sterilization is carried out at 121° C. with clean steam using an Autoclave that is validated for cGMP synthesis.

These particulate delivery vehicles, having been targeted to desired destination can be used as contrast agents for ultrasonic imaging for MRI imaging, for drug delivery, for diagnosis and/or therapy of using radionuclides, and the like. The particulate delivery vehicles are generally supplied in the form emulsions and are useful in the methods of the invention that include imaging of tissues and/or drug delivery.

Kits

The emulsions of the invention may be prepared and used directly in the methods of the invention, or the components of the emulsions may be supplied in the form of kits. The kits may comprise the pre-prepared targeted composition containing all of the desired ancillary materials in buffer or in lyophilized form. Alternatively, the kits may include a form of the emulsion which lacks the targeting ligand which is supplied separately. Under these circumstances, typically, the emulsion will contain a reactive group, such as a maleimide group, at the terminus of the linker distal to the anchor which, when the emulsion is mixed with the targeting agent, effects the binding of the targeting agent to the emulsion itself. A separate container may also provide additional reagents useful in effecting the coupling. Alternatively, the emulsion may contain reactive groups which bind to linkers coupled to the desired component to be supplied separately which itself contains a reactive group. A wide variety of approaches to constructing an appropriate kit may be envisioned. Individual components which make up the ultimate emulsion may thus be supplied in separate containers, or the kit may simply contain reagents for combination with other materials which are provided separately from the kit itself.

A non-exhaustive list of combinations might include: emulsion preparations that contain, in their lipid-surfactant layer, an ancillary component such as a fluorophore or chelating agent and reactive moieties for coupling to the targeting agent at the linker terminus distal to the anchor; the converse where the emulsion contains the compound of formula (1) is coupled to targeting agent and contains reactive groups for coupling to an ancillary material; emulsions which contain both the compound of formula (1) and a chelating agent but wherein the metal to be chelated is either supplied in the kit or independently provided by the user.

Applications

The emulsions and kits for their preparation are useful in the methods of the invention which include imaging of tissues containing high expression levels of target, and where tissues with such expression levels are undesirable, treatment.

When diagnostic radiopharmaceuticals are administered in the emulsion by intravenous injection, usually in saline solution, this is at a dose of 1 to 100 mCi per 70 kg body weight, or preferably at a dose of 5 to 50 mCi. Imaging is performed using known procedures.

When therapeutic radiopharmaceuticals are administered in the emulsion by intravenous injection, usually in saline solution, this is at a dose of 0.01 to 5 mCi per kg body weight, or preferably at a dose of 0.1 to 4 mCi per kg body weight. For comparable therapeutic radiopharmaceuticals, current clinical practice sets dosage ranges from 0.3 to 0.4 mCi/kg for Zevalin™ to 1-2 mCi/kg for OctreoTher™, a labeled somatostatin peptide. For such therapeutic radiopharmaceuticals, there is a balance between tumor cell kill vs. normal organ toxicity, especially radiation nephritis. At these levels, the balance generally favors the tumor cell effect. These dosages are higher than corresponding imaging isotopes.

Magnetic resonance imaging contrast agents may be used in a similar manner as other MRI agents as described in U.S. Pat. No. 5,155,215; U.S. Pat. No. 5,087,440; Margerstadt, et al., *Magn. Reson. Med.* (1986) 3:808; Runge, et al., *Radiology* (1988) 166:835; and Bousquet, et al., *Radiology* (1988) 166: 693. Other agents that may be employed are those set forth in U.S. patent publication 2002/0127182 which are pH sensitive and can change the contrast properties dependent on pulse. Generally, sterile aqueous solutions of the contrast agents are administered to a patient intravenously in dosages ranging from 0.01 to 1.0 mmoles per kg body weight.

A particularly preferred set of MRI chelating agents includes 1,4,7,10-tetraazacyclododecane-1,4,7,10-tetraacetic acid (DOTA) and its derivatives, in particular, a methoxybenzyl derivative (DOTA-NCS) comprising an isothiocyanate functional group which can then be coupled to the amino group of phosphatidyl ethanolamine or to a peptide derivatized form thereof. Derivatives of this type are described in U.S. Pat. No. 5,573,752, incorporated herein by reference. Other suitable chelating agents are disclosed in U.S. Pat. No. 6,056,939, also incorporated herein by reference.

The DOTA isocyanate derivative can also be coupled to the lipid/surfactant directly or through a peptide spacer. The use of gly-gly-gly as a spacer is illustrated in the reaction scheme below. For direct coupling, the DOTA-NCS is simply reacted with PE to obtain the coupled product. When a peptide is employed, for example a triglycyl link, phosphoethanolamine (PE) is first coupled to t-boc protected triglycine. Standard coupling techniques, such as forming the activated ester of the free acid of the t-boc-triglycine using diisopropyl carbodiimide (or an equivalent thereof) with either N-hydroxy succinimide (NHS) or hydroxybenzotriazole (HBT) are employed and the t-boc-triglycine-PE is purified.

Treatment of the t-boc-triglycine-PE with trifluoroacetic acid yields triglycine-PE, which is then reacted with excess DOTA-NCS in DMF/CHCl₃ at 50° C. The final product is isolated by removing the solvent, followed by rinsing the remaining solid with excess water, to remove excess solvent and any un-reacted or hydrolyzed DOTA-NCS.

The following example is intended to illustrate but not limit the invention.

Example 1

Preparation of the Compound of Formula (2)

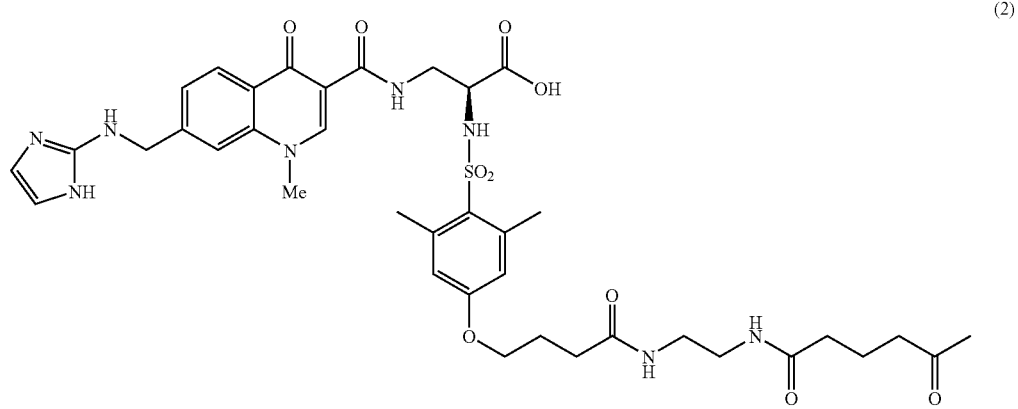

(2)

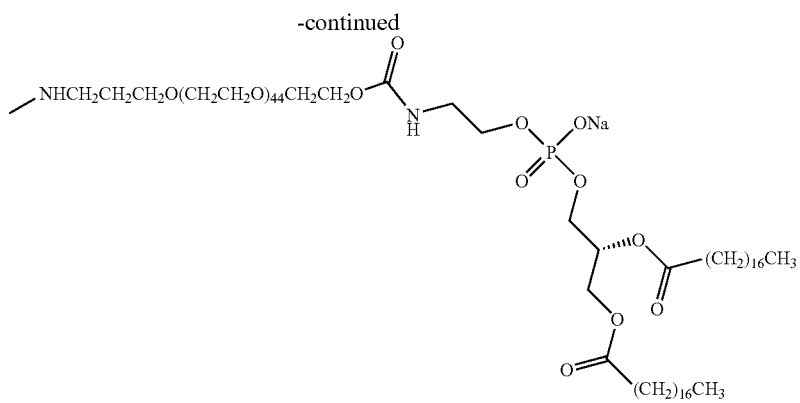
The following schemes show the overall method of synthesis:
Synthetic Pathway for $\alpha_v\beta_3$-Targeting Ligand Intermediate 12:
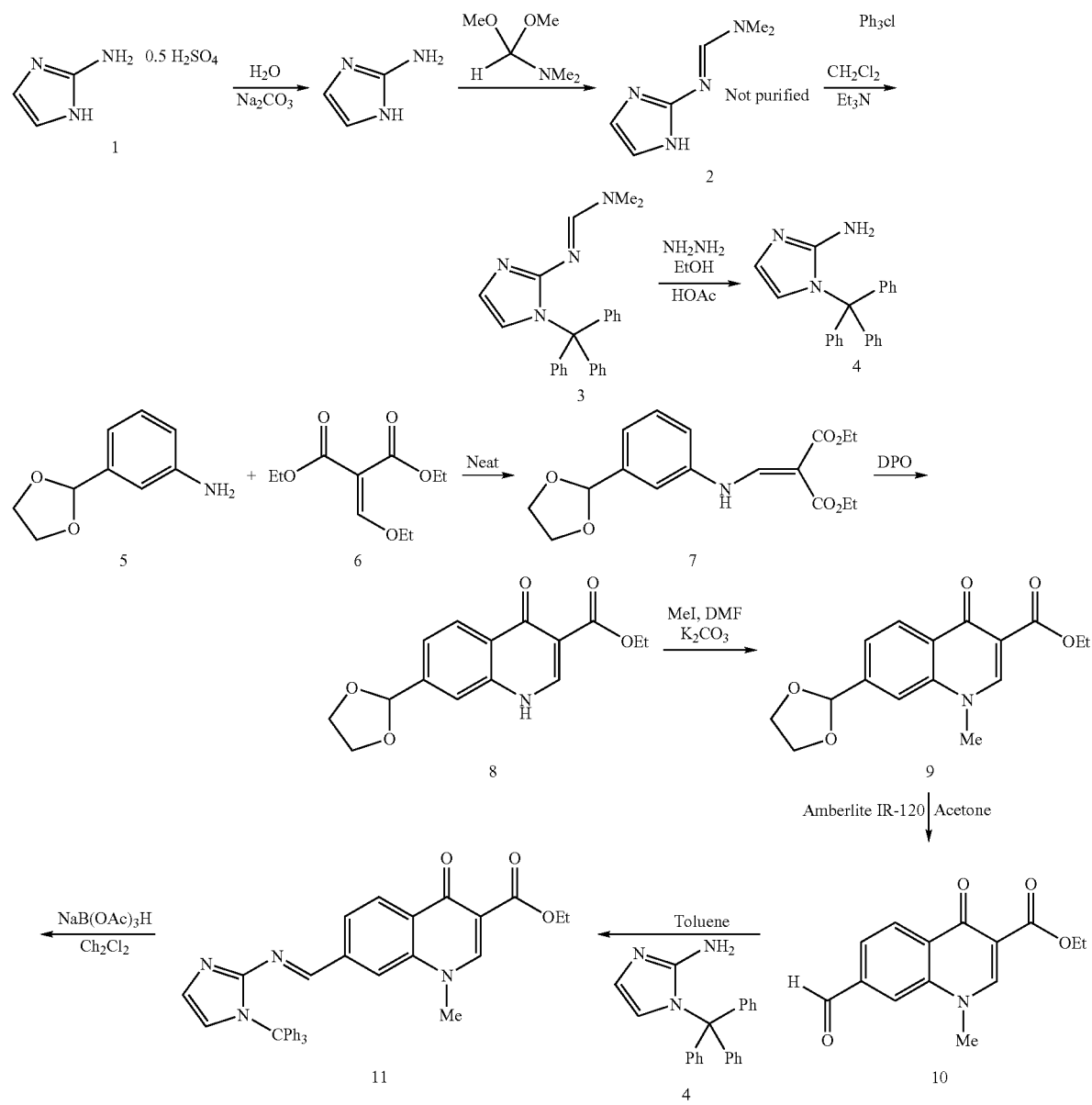

-continued
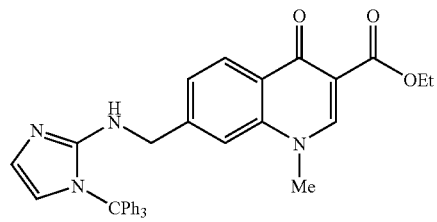
12
Synthetic Pathway for $\alpha_v\beta_3$-Targeting Ligand Intermediate 22:
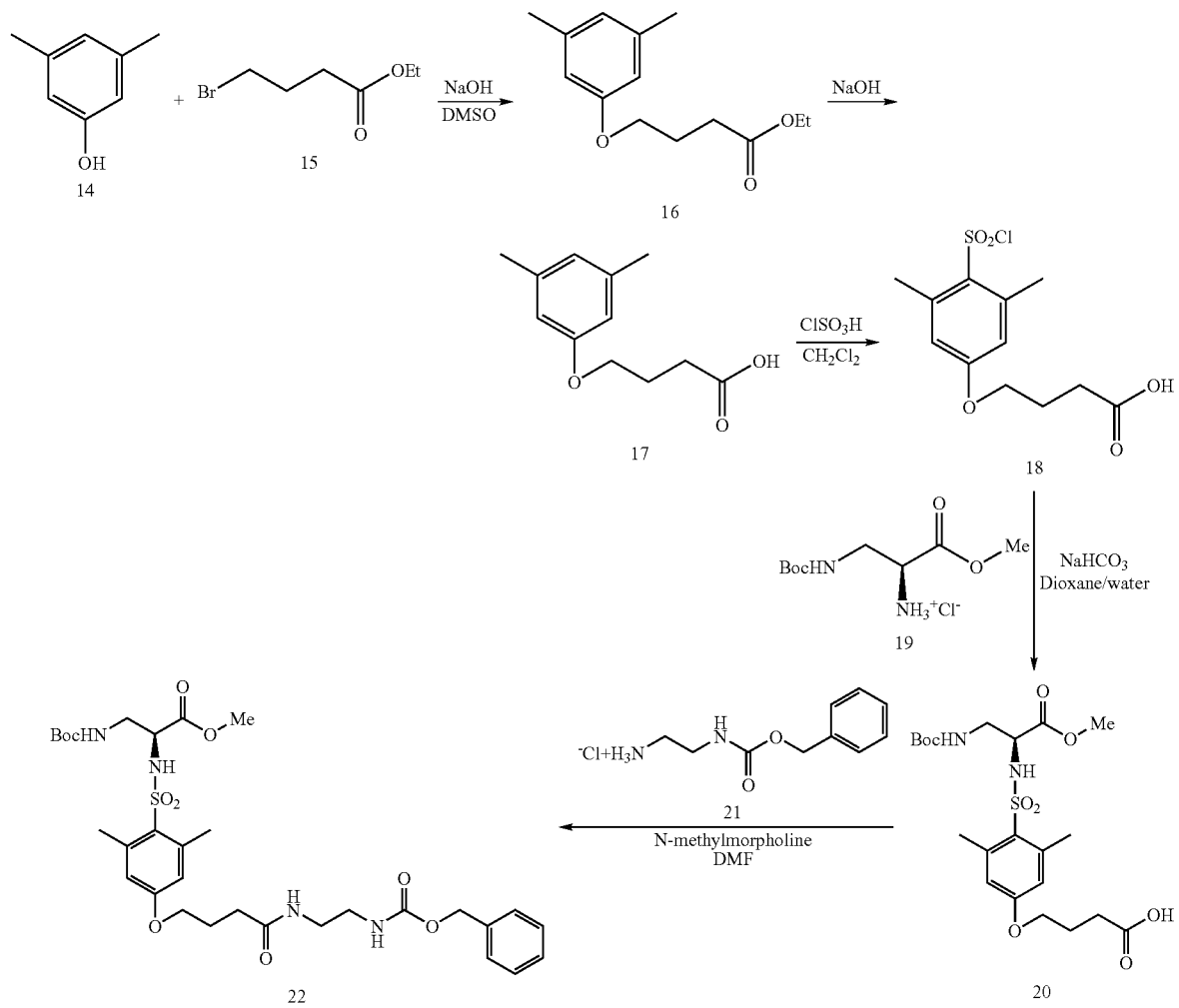
Synthetic Pathway for $\alpha_v\beta_3$-Targeting Ligand 29:

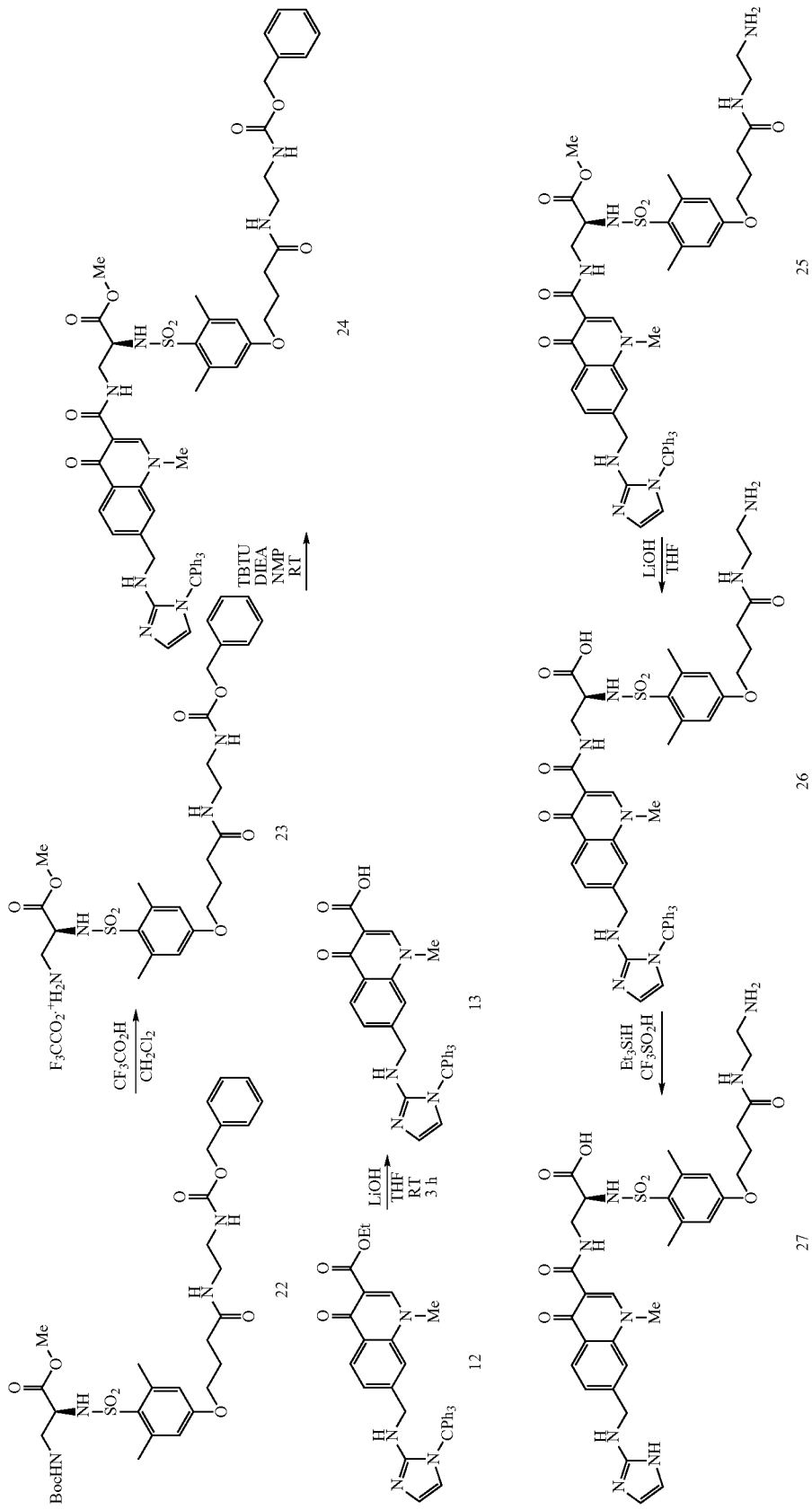

-continued
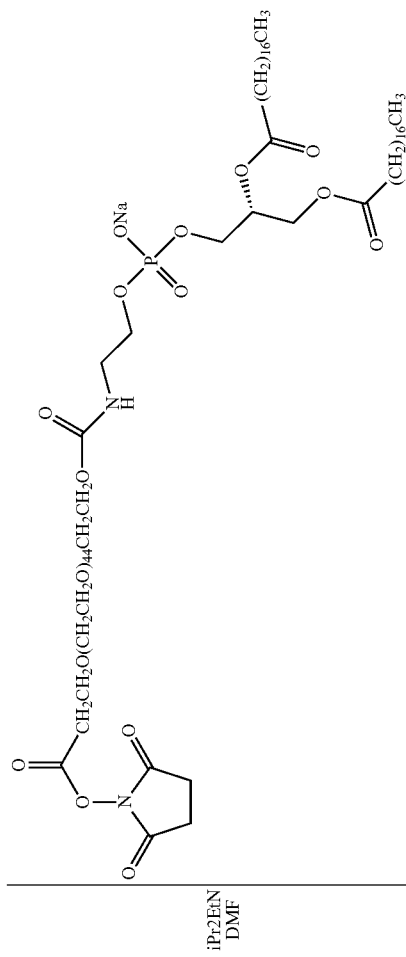
28
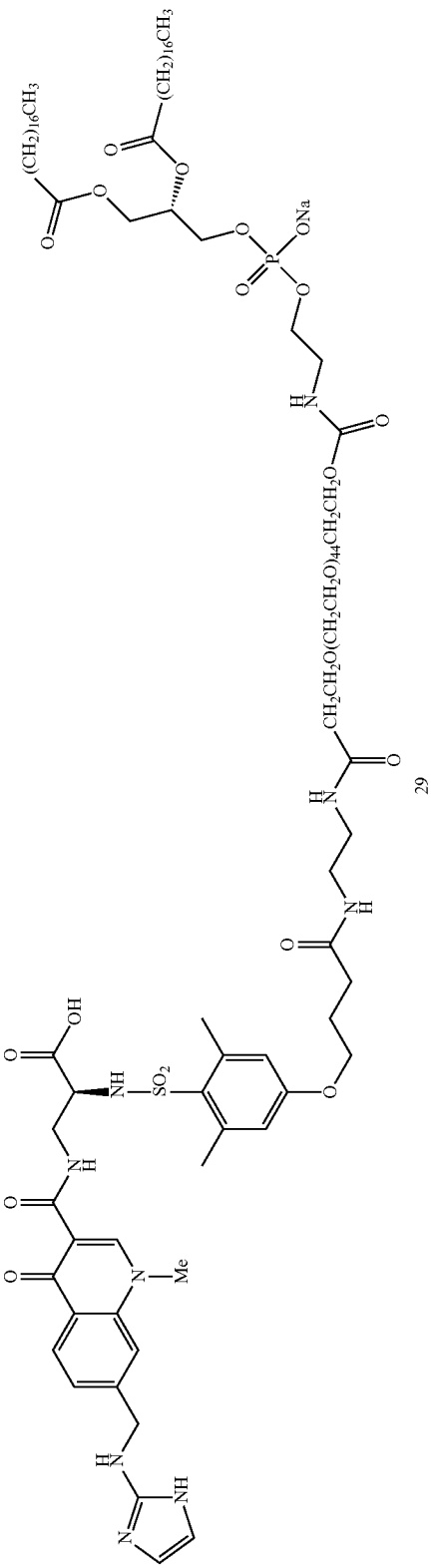
29

In more detail, steps are carried as follows:

STEP 1

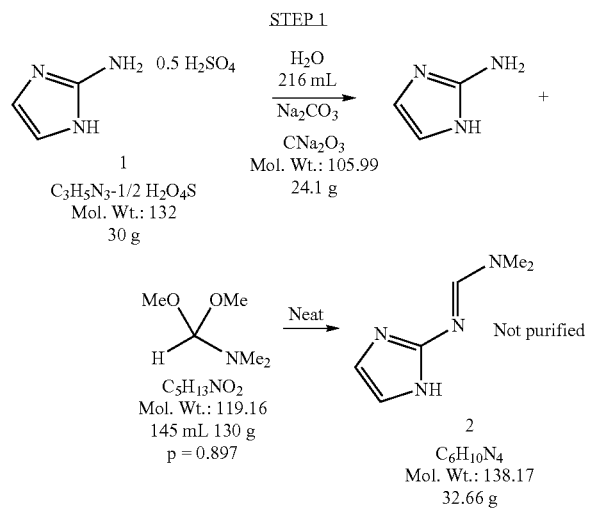

2-[(dimethylamino)methylene]aminoimidazole (2)

2-Aminoimidazole hemisulfate (1, 30 g, 227 mmol) (Aldrich) was dissolved in water (216 mL) and sodium carbonate (24.1 g, 227 mmol) was added. The solution was stirred at room temperature for 15 minutes. Water was removed in vacuo and the residue was triturated with absolute ethanol (85 mL), the mixture filtered and solvent removed in vacuo. The residue was used immediately.

To the crude 2-aminoimidazole (18.2 g) was added dimethylformamide dimethyl acetal (145 mL) (Aldrich) and stirred at room temperature overnight. The reagent was removed in vacuo to give crude 2 (32.66 g) which was taken on to the next step (tritylation) without further purification.

Product I.D.: $^1$H NMR, FT-IR, LC/MS

STEP 2

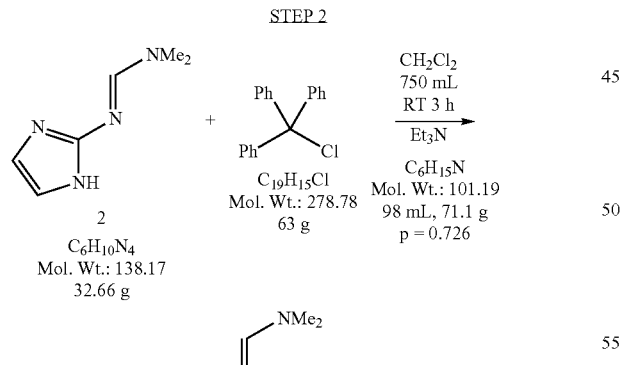

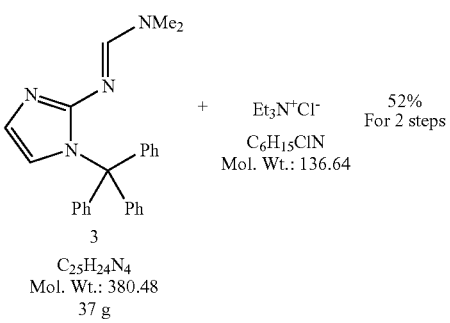

1-trityl-2-[(dimethylamino)methylene]aminoimidazole (3)

To the crude 2-[(dimethylamino)methylene]aminoimidazole (2) was added methylene chloride (750 mL), triethylamine (98 mL, 700 mmol) and trityl chloride (62.98 g, 226 mmol) (Aldrich). The reaction mixture was stirred at room temperature for 3 hrs. Solvent was removed in vacuo and the crude 3 was crystallized from methanol.

Crude 3 was re-crystallized from hot methanol (450 mL) and the solution was allowed to cool to room temperature to obtain pure product (3) as a light yellow solid which was filtered, washed with 100 mL of MTBE and dried under vacuum for 1 hr (37 grams).

Mother liquor was concentrated and upon seeding with purified 3 and stirring a second crop of 7.64 g of 3 was isolated. Total yield was 44.64 g (52%, 2 steps).

In process assay: HPLC

Product I.D.: $^1$H NMR, FT-IR, LC/MS

STEP 3

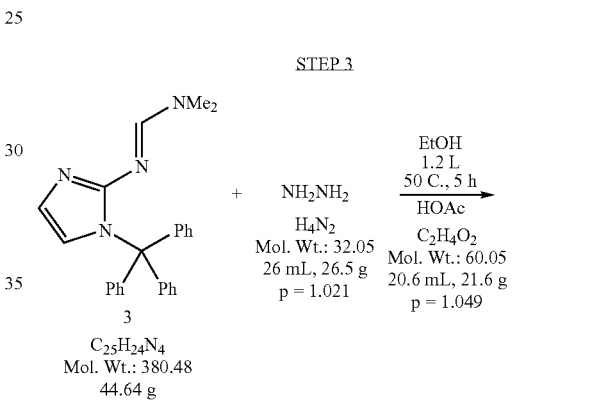

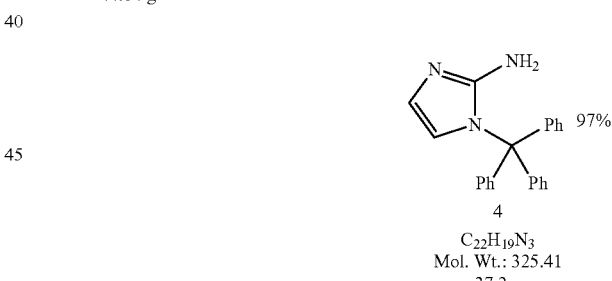

1-trityl-2-aminoimidazole (4)

To 3 (44.64 g, 117 mmol) was added reagent grade ethanol (1200 mL), glacial acetic acid (20.65 mL) and hydrazine (26 mL). The reaction mixture was stirred at 50° C. for 5 hrs. Solvent was removed and to the crude product was added methylene chloride (1,500 ml) and 1 N sodium hydroxide (67 ml) with stirring at room temperature for 15 minutes. The two resulting layers were separated and the organic layer was washed with brine (2×300 mL), dried over anhydrous sodium sulfate, filtered and solvent removed in vacuo to obtain 1-trityl-2-aminoimidazole, 4 (37.2 g, 97%). M.p. 196-199° C.

In process assay: HPLC

Product I.D.: $^1$H NMR, FT-IR and LC/MS

STEP 4

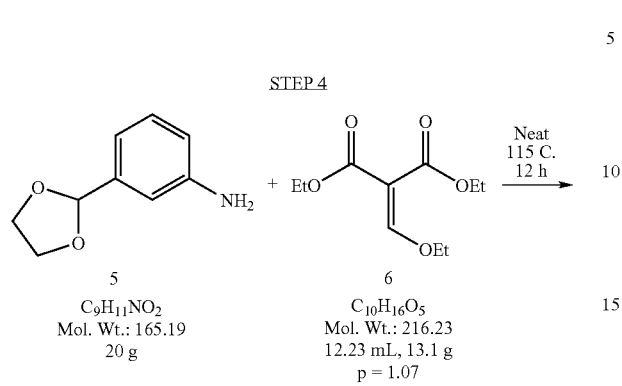

Diethyl (((3-(1,3-dioxolan-2-yl)phenyl)amino)methylene)malonate (7)

A mixture of compounds 5 (Alfa Aesar) and 6 (Aldrich) was heated to 115° C. overnight in a 100 mL 1-neck round bottom flask fitted with a Dean-Stark trap, after which it was allowed to cool to room temperature. Rotary evaporation (1 h/40° C.) removes most of the residual EtOH. The product, 7 (20.30 g, quantitative yield) is a thick oil that solidifies in time, in the freezer or after vigorous mortaring. Analysis ($^1$H NMR) indicates that it is of high enough purity to be used as such in the next step.

In Process assay: HPLC

Product I.D.: $^1$H NMR

STEP 5

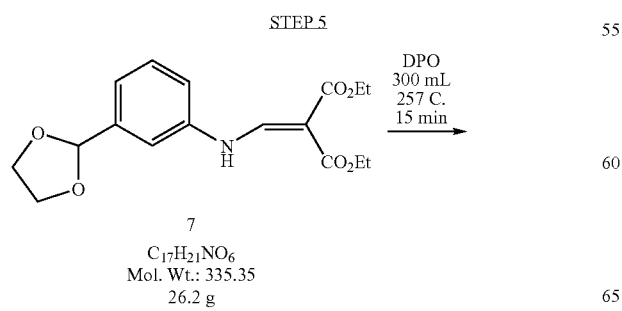

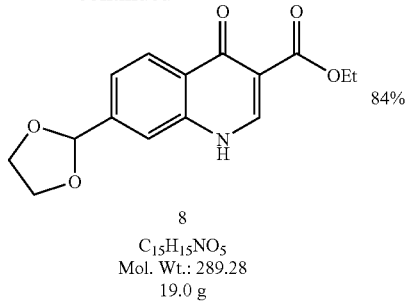

Ethyl 7-(1,3-dioxolan-2-yl)-4-oxo-1,4-dihydroquinoline-3-carboxylate (8)

Compound 7 was added to 300 mL diphenyl ether (Aldrich) that had been preheated to 250° C. in a 1 L 3-neck round bottom flask. The temperature dropped to ca 240° C. for a brief time (1-2 min), after which it was brought up to 257° C. and maintained at 255-260° C. for 15 min, as the color darkened and evolution of EtOH vapor was observed. Upon cooling to room temperature, some ppt separated, but the mixture was extremely thick. The mixture was diluted 1:4 with hexane, and more ppt separated. The ppt was filtered, washed 3× hexane, and dried to afford 19.02 g product (84%) 8. Analysis ($^1$H NMR) showed that the product was of high enough purity to be used as such in the next step.

In Process assay: HPLC

Product I.D.: $^1$H NMR, FT-IR, LC/MS

STEP 6

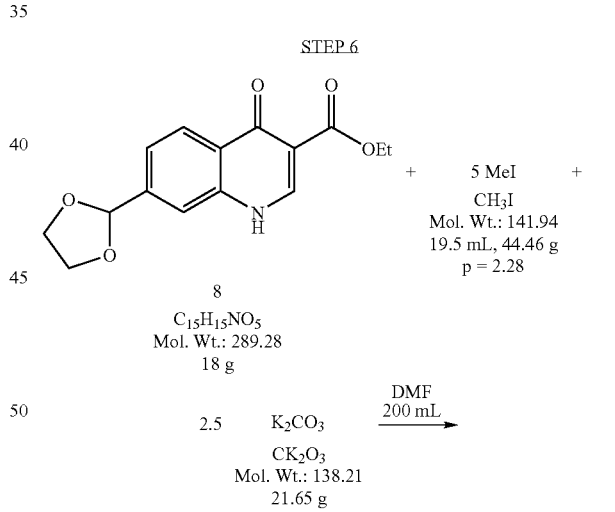

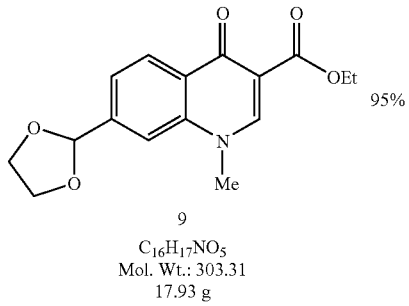

Ethyl 7-(1,3-dioxolan-2-yl)-1-methyl-4-oxo-1,4-dihydroquinoline-3-carboxylate (9)

Compound 8 was dissolved in anhydrous DMF (Aldrich) in a 500 mL 1-neck round bottom flask. Anhydrous potassium carbonate (EM Science) was added and the mixture was stirred for 15 min. After addition of iodomethane (Aldrich), the mixture was stirred at room temperature overnight, after which it was concentrated and partitioned between CH$_2$Cl$_2$ and aq. sodium thiosulfate. The CH$_2$Cl$_2$ layer was rinsed with brine, dried over anhydrous sodium sulfate, filtered, and concentrated to 19.30 g crude 9 (brownish solid). $^1$H NMR spectrum was satisfactory; however, TLC (MeOH:DCM 1:9) shows small amounts of lower polarity impurities and some high polarity impurities (possibly largely inorganic). Attempts to purify via re-precipitation from THF/water or CH$_2$Cl$_2$/hexane were unsatisfactory. Chromatography on a silica gel plug (gradient 1-2-4-6-10% methanol in CH$_2$Cl$_2$) provided purified product (17.93 g, 95% yield).

In Process assay: HPLC
Product I.D.: $^1$H NMR, FT-IR, LC/MS

STEP 7

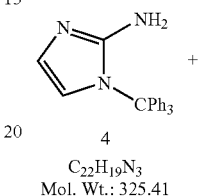

9
C$_{16}$H$_{17}$NO$_5$
Mol. Wt.: 303.31
6.07 g

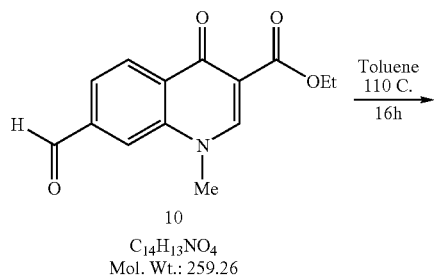

10
C$_{14}$H$_{13}$NO$_3$
Mol. Wt.: 245.27
4.2 g

Ethyl 7-formyl-1-methyl-4-oxo-1,4-dihydroquinoline-3-carboxylate (10)

Compound 9 was dissolved in acetone (EMCO), at 60° C. in a 1 L, 1-neck round bottom flask. Pre-washed Amberlite IR-120 resin (Aldrich) was added with the water and the mixture was stirred at 60° C. for 40 minutes; aliquots were removed at 20 min (MCLS0995-078-1) and 40 min. HPLC analysis of the aliquots revealed that the de-protection of the aldehyde was complete in 20 minutes. The mixture was removed from the heating bath, filtered, and concentrated to ca. 40% of the initial volume under rotary evaporation (removal of acetone). The resulting aqueous suspension was partitioned between CH$_2$Cl$_2$ and sat. aq. sodium bicarbonate. The aqueous layer was extracted 2×CH$_2$Cl$_2$. The combined organic layers were washed with brine, dried over anhydrous sodium sulfate, filtered and concentrated to afford product 10 (4.20 g, 81% yield).

In Process assay: HPLC
Product I.D.: $^1$H NMR, FT-IR, LC/MS

STEP 8

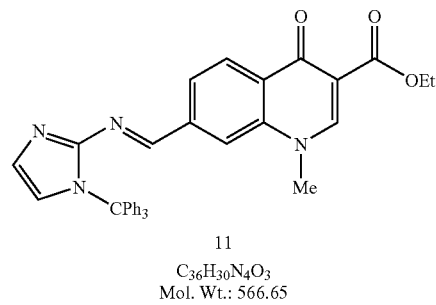

11
C$_{36}$H$_{30}$N$_4$O$_3$
Mol. Wt.: 566.65

STEP 9

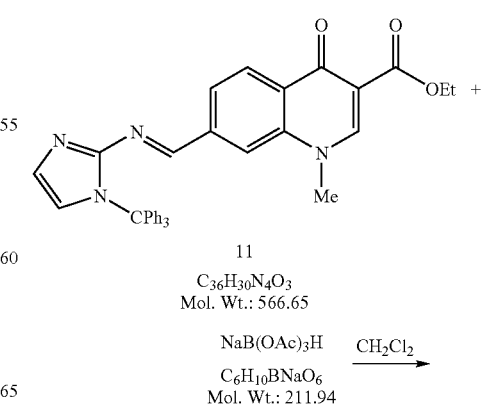

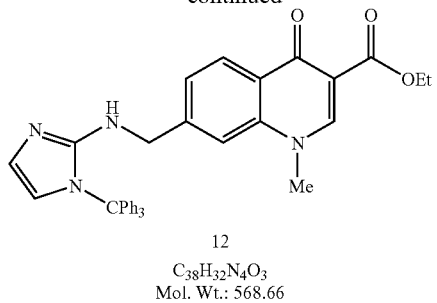

12
C₃₈H₃₂N₄O₃
Mol. Wt.: 568.66

Ethyl 7-(1-(triphenylmethyl-1H-imidazol-2-ylamino)methyl)-1-methyl-4-oxo-1,4-dihydroquinoline-3-carboxylate (11)

Compounds 4 and 10 were stirred in toluene, under nitrogen, at 110° C., overnight, in a 1 L, 1-neck round bottom flask fitted with condenser and a Dean-Stark trap. After cooling to room temperature, the mixture containing the intermediate imine (11) was concentrated and analyzed (¹H NMR, FT-IR, UV).

The mixture was re-dissolved in 250 mL CH₂Cl₂. Sodium triacetoxyborohydride (6 eq.) (Aldrich) was added and the resulting mixture was stirred at room temperature overnight. An aliquot was removed and worked-up as follows: The solvent was evaporated; the residue was partitioned between ethyl acetate (EA) and aq. potassium carbonate/brine mixture. The aq. layer was re-extracted with EA. The combined EA layers were washed with brine, dried over anhydrous sodium sulfate, filtered, and concentrated to afford 12. The analytical results (HNMR; other: IR, UV) indicated that the reduction was complete. ¹H NMR shows some AcOH traces, so the pH of the aq. layer was re-checked to be found as ca. 5-6 (quite likely, larger excess carbonate may have been required to overcome the buffering effect of the AcOH/AcO⁻ couple).

The bulk of the mixture was worked-up in the same manner as the aliquot, with the difference that it was made sure enough potassium carbonate solution was used to ensure a basic pH (8-9). The separation was in this case more difficult and lengthier.

The crude mixture was chromatographed on silica gel (1-10% gradient of MeOH in CH₂Cl₂). Fractions 7-10 contained product (12, 5 g, 67.1% yield).

In Process assay: HPLC
Product I.D.: ¹H NMR, ¹³C NMR, FT-IR, LC/MS, residual solvent analysis, elemental analysis, loss on drying
C of A generated for this intermediate

STEP 10

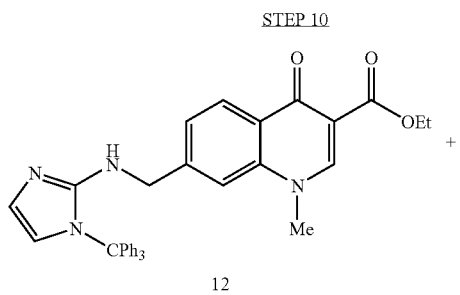

12
C₃₆H₃₂N₄O₃
Mol. Wt.: 568.66

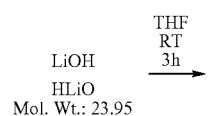

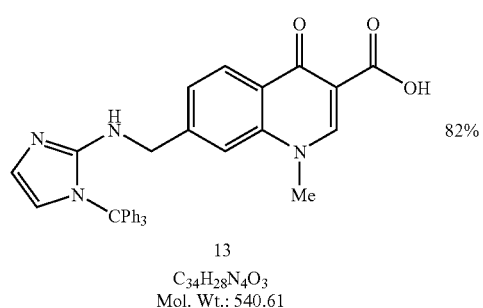

13
C₃₄H₂₈N₄O₃
Mol. Wt.: 540.61

7-(1-(triphenylmethyl-1H-imidazol-2-ylamino)methyl)-1-methyl-4-oxo-1,4-dihydroquinoline-3-carboxylic acid (13)

Compound 12 was dissolved in THF. Aq. LiOH was added and the mixture was stirred at room temperature for 3 h, after which it was diluted with water, concentrated until THF was removed (foaming and pp occur) and acidified with HCl to pH 4 (intense foaming; more pp). The precipitate was separated, washed with water, and dried to afford 13 (product, 3.40 g, 96.5% purity by HPLC, LC-MS, 81.7% yield). ¹H NMR analysis is more consistent with an over-protonated species, Tr-Im-N(H₂)⁺—CH₂—Ar than with the free amine form. Elemental analysis confirms partial formation of alkyl-ammonium chloride salts at some of the amine sites. (Material used as is in Step 17)

In Process assay: HPLC
Product I.D.: ¹H NMR, FT-IR, LC/MS

STEP 11

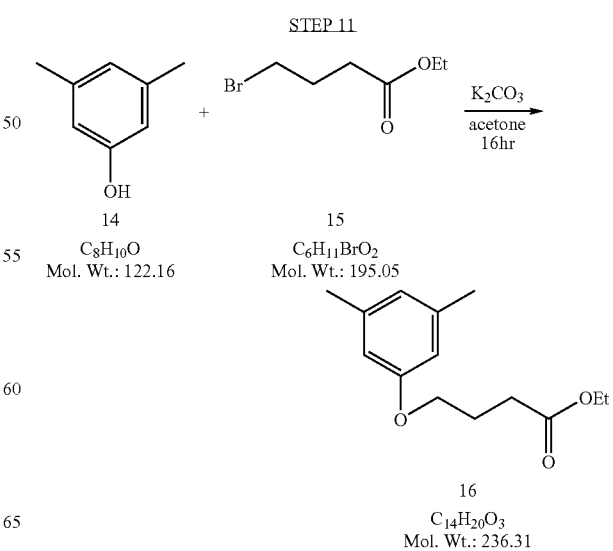

14                    15
C₈H₁₀O              C₆H₁₁BrO₂
Mol. Wt.: 122.16    Mol. Wt.: 195.05

16
C₁₄H₂₀O₃
Mol. Wt.: 236.31

STEP 12

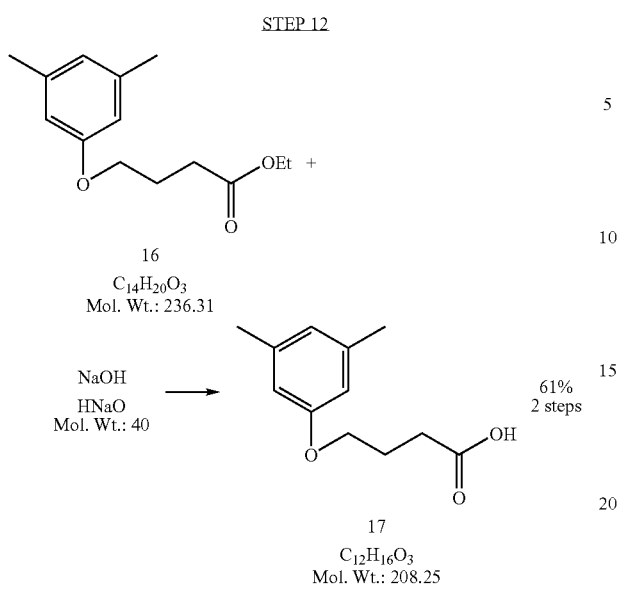

3,5-Dimethylphenoxybutanoic Acid (17)

A 500 mL 3 neck flask was charged with 14 and NaOH under a nitrogen purge. With mechanical stirring the mixture was heated to melt the phenol and then 100 mL of DMSO was added. The solution was heated to 125° C. then cooled to 100° C. At 100° C. 15 (Aldrich) was added over 3 minutes (exotherm of 8° C.) and then the temperature was raised to 125° C. for 30 min. The reaction was allowed to cool to 90° C. and 100 mL H$_2$O added. The mixture was allowed to cool to 60° C. and 18 mL of 50% NaOH (aq) was added with an exotherm to 70° C. at which temperature the reaction mass was held for 15 min. The reaction was cooled to 40° C. and 250 mL water was added followed by the addition of conc. HCl until a pH of 8 was achieved. The reaction mass was cooled to ambient and then extracted 4×50 mL MTBE. The aqueous layer was acidified to pH 1 using conc. HCl (ca. 20 mL) at which point crystallization began.

The solid was recovered via filtration and the solid washed with 10 mL cyclohexane. The residue was then recrystallized from 80 mL cyclohexane. The recovered product was washed with 15 mL cyclohexane and dried in vacuum oven at 30° C. giving 26.3 g of 17 (62% of 99.7% purity by HPLC).

In process assay: HPLC
Product I.D.: $^1$H NMR, FT-IR, LC/MS

STEP 13

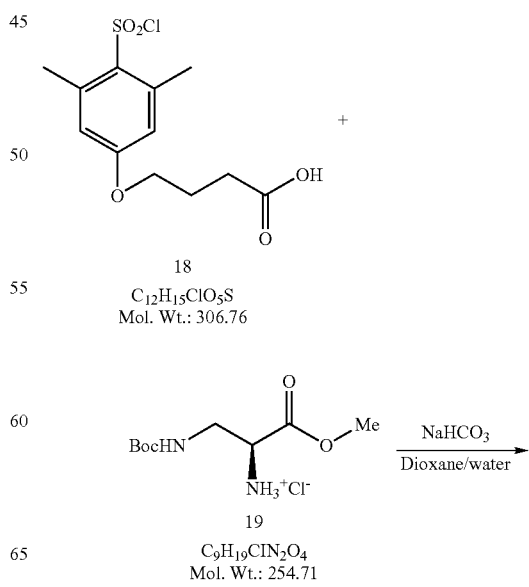

4-(Chlorosulfonyl)-3,5-dimethylphenoxybutanoic acid (18)

A 500 mL 3-neck flask was charged with 3,5-dimethylphenoxybutanoic acid (17) (25 g, 120 mmol) and CH$_2$Cl$_2$ (100 mL). This solution was cooled to −27° C. with mechanical stirring then chlorosulfonic acid (42 g, 360 mmol) was added dropwise over 30 min (temperature reached a max. of −20° C.). The material was stirred for an additional 1 hr at −25° C. then NaHCO$_3$ (20 g, 238 mmol) was added to the reaction mixture. The reaction mixture was then added to 150 g of ice. The reaction mixture was then extracted into EtOAc (750 mL), dried over Na$_2$SO$_4$ (10 g), filtered and then concentrated in vacuo. Two triturations of the crude product with MTBE at 5° C. (50 mL then 25 mL) gave 20.0 g 18 (54% yield).

In process assay: HPLC
Product I.D.: $^1$H NMR, FT-IR, LC/MS

STEP 14

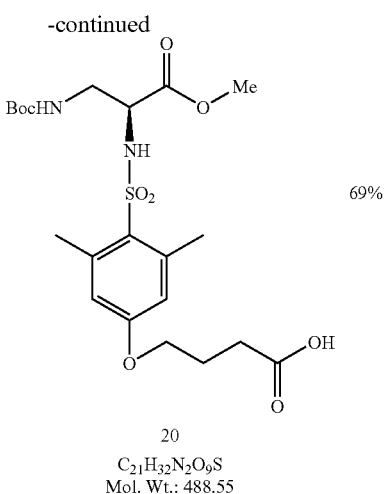

4-(4-(((2-(((tert-Butoxy)carbonylamino)-1-(methoxy-carbonyl)ethyl) amino)sulfonyl)-3,5-dimethylphenoxy)butanoic acid (20)

A solution of the 4-(chlorosulfonyl)-3,5-dimethylphenoxybutanoic acid, 18 (2.50 g, 8.1 mmol) in dioxane (60.0 g) was added dropwise over a period of about 45 minutes to a mixture of H-Dap(Boc)-OMe.HCl (19) (1.66 g, 6.5 mmol) (Bachem) and NaHCO$_3$ (8.21 g, 97.7 mmol) in water (20.0 g) at rt. Two hours after completion of the addition, the reaction mixture was concentrated in vacuo then water and citric acid (12.50 g, 10.0 eq.) were added. The crude product was extracted with EtOAc and the EtOAc layer was washed once with water. Concentration of the EtOAc layer gave 2.75 g of 20 (87% yield based on 19, 69% based on 18).

Modification on Scale Up

A slurry of H-Dap(Boc)-OMe.HCl (19) (8.0 g, 31.4 mmol) and NaHCO$_3$ (38.6 g, 460 mmol) in 140 mL dioxane/28 mL H$_2$O was cooled to 5° C. with an ice bath. To this slurry was added a solution of the 4-(chlorosulfonyl)-3,5-dimethylphenoxybutanoic acid, 18 (14.0 g 46 mmol) in dioxane (140 mL) dropwise over a period of 75 minutes. After an additional 2 hr the reaction mixture was filtered and the filtrate concentrated in vacuo. To the residue was added water (total volume of 420 mL) and then this was extracted with 75 mL MTBE. The aqueous phase was made acidic (pH=4) using 3 N HCl (aq.) then extracted with EtOAc (300 mL). The EtOAc extract was dried over Na$_2$SO$_4$, filtered and concentrated in vacuo leaving 10.2 g of desired product, 20 (20.9 mmol, 66.5% based on 19, 45% based on 18).

In process assay: HPLC

Product I.D.: $^1$H NMR, FT-IR, LC/MS, optical rotation, chiral HPLC

STEP 15

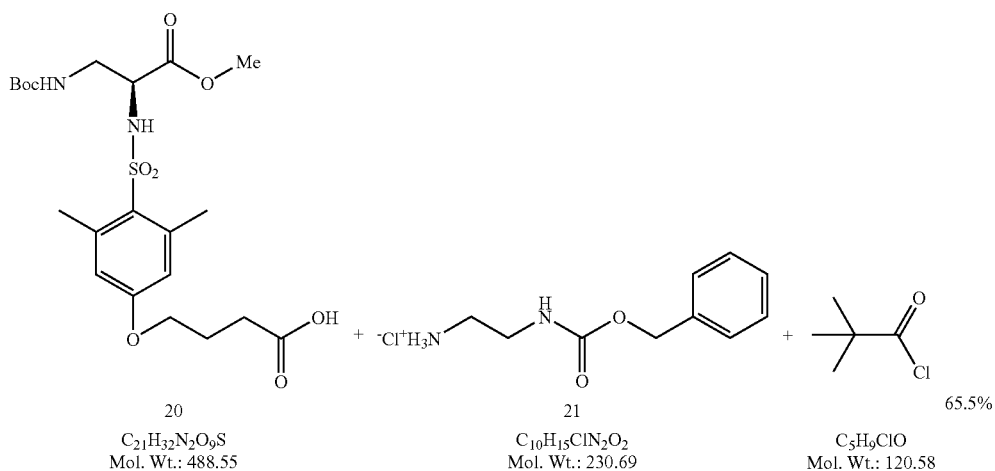

-continued

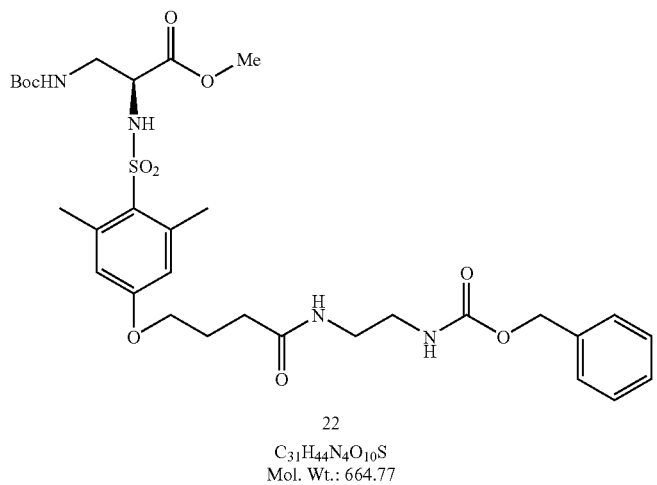

22
C$_{31}$H$_{44}$N$_4$O$_{10}$S
Mol. Wt.: 664.77

Methyl (2S)-3-[(tert-butoxy)carbonylamino]-2-[({2,6-dimethyl-4-[3-(N-{2-[(phenylmethyoxy)carbonylamino]ethyl}carbamoyl)propoxy]phenyl}sulfonyl)amino]propanoate (22)

To a solution of the crude phenoxybutanoic acid (20) from the previous reaction (2.75 g) in CH$_2$Cl$_2$ (150 mL) cooled in an ice water bath was added 4-methylmorpholine (0.89 g, 8.8 mmol) and then trimethylacetyl chloride (1.06 g, 8.8 mmol). The reaction mixture was allowed to warm to rt. After 1 h, the reaction mixture was concentrated in vacuo then DMF (100 mL) was added and this was also removed in vacuo (to remove any unreacted trimethylacetyl chloride, bp 105-106° C.). The crude product was redissolved in CH$_2$Cl$_2$ (150 mL) and a solution of benzyl N-(2-aminoethyl)carbamate hydrochloride, 21 (1.52 g, 6.6 mmol) and 4-methylmorpholine (1.11 g, 11.0 mmol) in DMF was added. After 1 h, the reaction mixture was concentrated in vacuo and partitioned between EtOAc and water. After separation of the layers, the EtOAc solution was washed with dilute NaHCO$_3$ and water. The EtOAc solution was concentrated in vacuo to give the crude product. This material was purified by chromatography (97:3 EtOAc/MeOH) to give 2.80 g of product 22.

Addition of ether to this material caused the oil to crystallize. Filtration of the resulting solid gave 2.44 g of purified 22 (65.5%).

Alternate Method, Used on Larger Scale 20 (8.20 g, 16.8 mmol) Was dissolved in DMF (70 mL, Dried over 3A molecular sieves). Diisopropyl ethyl amine (8.68 g, 67.1 mmol) was added and the mixture was stirred under nitrogen. The mixture was cooled in a cool water bath then HBTU, O-benzotriazol-1-yl-N,N,N',N'-tetramethyluronium hexafluorophosphate (7.64 g, 20.1 mmol) was added in portions at a temperature below 17° C. The mixture was further stirred for 20 minutes. A solution of benzyl N-(2-aminoethyl)carbamate hydrochloride, 21, (4.65 g, 20.1 mmol) in DMF (21 mL, dried over 3A molecular sieves) was added drop wise at a temperature below 17° C. The solution was further stirred for 30 minutes and was allowed to warm to ambient temperature. The reaction solution was then evaporated at 60° C. and 10 mbar. This gave a residue of 33.8 g. The residue was dissolved in dichloromethane (120 mL). The mixture was washed twice with 0.1 M HCl (aq.), 20 mL each. The mixture was then washed three times with 10% NaHCO$_3$, 20 mL each. Evaporation at 50° C. and 10 mbar gave 13.8 g residue.

The residue was dissolved in methylene chloride (15 mL) and filtered through silica gel 60 (100 g, size 0.015-0.040 mm, Merck). Dry Column Vacuum Chromatography technique was applied. The silica was eluted with eluent from pure ethyl acetate to a mixture ethylacetate with 5% methanol in small increments. Each with a 50 ml portions. Fractions 7-11 were combined as judged pure from TLC analysis. Evaporation gave 6.3 g foaming oil that solidified up on cooling (56%). Purity HPLC 254 nm 97.7%.

In Process assay: HPLC

Product I.D.: $^1$H NMR, $^{13}$C NMR, FT-IR, LC/MS, residual solvent analysis, elemental analysis, loss on drying, optical rotation C of A Generated for this Intermediate

STEP 16

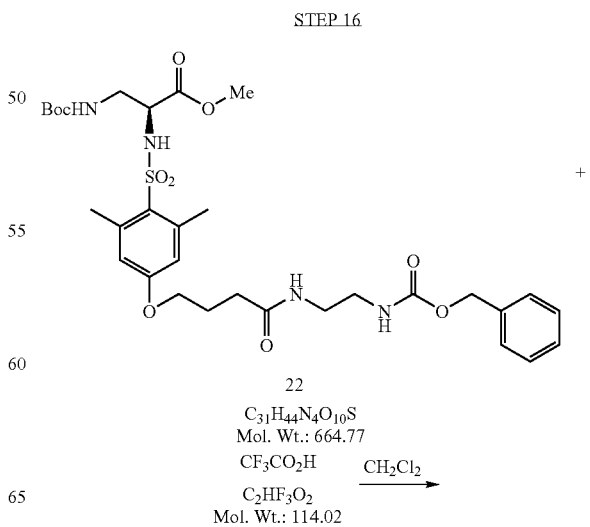

22
C$_{31}$H$_{44}$N$_4$O$_{10}$S
Mol. Wt.: 664.77
CF$_3$CO$_2$H   CH$_2$Cl$_2$ →
C$_2$HF$_3$O$_2$
Mol. Wt.: 114.02

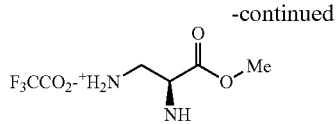

23
C$_{28}$H$_{36}$F$_3$N$_4$O$_{10}$S$^{2-}$
Mol. Wt.: 677.67

Methyl (2S)-3-amino-2-[({2,6-dimethyl-4-[3-(N-{2-[(phenylmethoxy)carbonylamino]ethyl}carbamoyl)propoxy]phenyl}sulfonyl)amino]propanoate trifluoroacetate (23)

Compound 22 was dissolved in CH$_2$Cl$_2$:Trifluoroacetic acid and stirred at room temperature for 30 min under nitrogen, after which it was concentrated, evaporated 6×CH$_2$Cl$_2$, and dried under high vacuum to afford 23 (pale yellow oil, 3.14 g). This was used as is in Step 17.

In process assay: HPLC
Product I.D.: $^1$H NMR, LC/MS, optical rotation

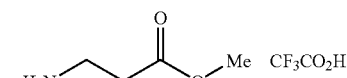

STEP 17

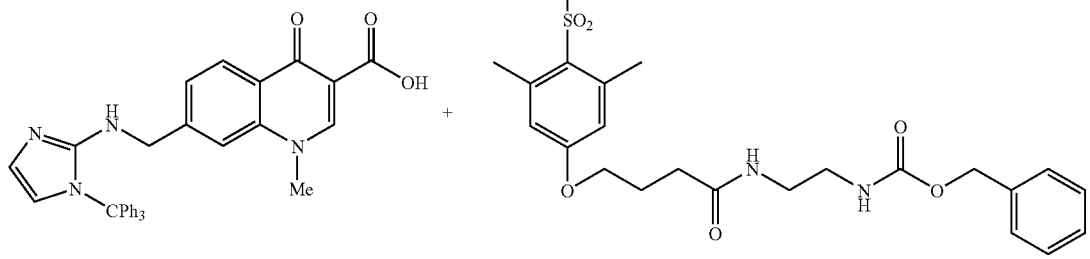

13
C$_{34}$H$_{28}$N$_4$O$_3$
Mol. Wt.: 540.61

23
C$_{28}$H$_{37}$F$_3$N$_4$O$_{10}$S
Mol. Wt.: 678.67

TBTU
DIEA
NMP
RT

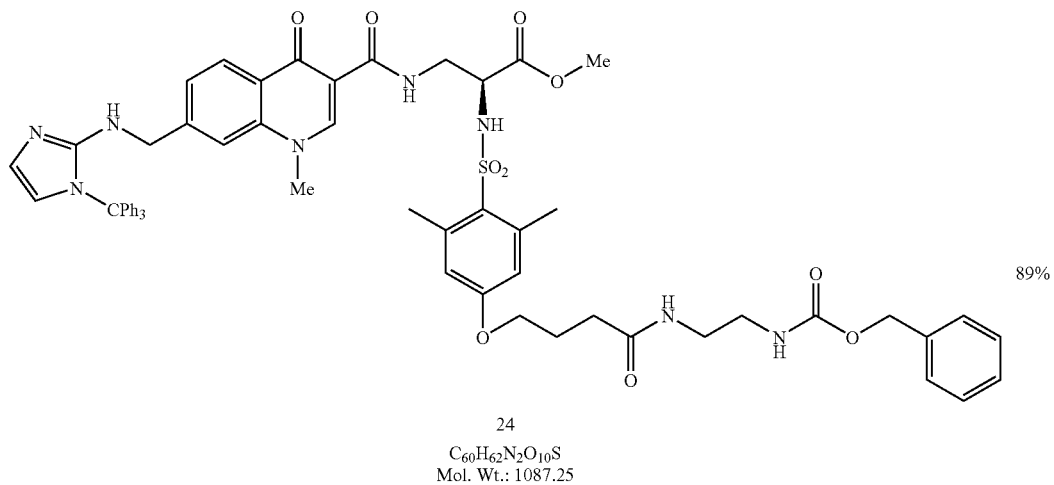

89%

24
C$_{60}$H$_{62}$N$_2$O$_{10}$S
Mol. Wt.: 1087.25

Procedure:

Glassware was dried in an oven at 110° C. and assembled under hot under nitrogen.

Under a nitrogen atmosphere, a magnetically stirred slurry of Acid 13 (5.15 g; 9.5 mmol) and diisopropylethyl-amine (16.5 mL; 94.7 mmol) in anhydrous N-methylpyrrolidinone (50 mL) was treated with O-benzotriazol-1-yl)-N,N-N',N'-tetramethyluronium tetrafluoroborate (3.65 g; 11.4 mmol) in one portion and chased with anhydrous NMP (15 mL). The slurry was stirred at ambient temperature (25° C.) for 15 minutes under nitrogen. A solution of the crude trifluoroacetate salt of amine 23 (8.9 g; 72% assay; 9.5 mmol) containing some residual trifluoroacetic acid (≈21.9 mmol by calculation) in anhydrous NMP (100 mL) was added dropwise over 62 minutes with a slight exotherm as the temperature rose from 25 to 28° C. The addition funnel was rinsed with anhydrous NMP (10 mL) and added to the reaction mixture. The clear, light amber solution was stirred at ambient temperature under nitrogen (3:55 pm) overnight. pH Paper dipped in the reaction mixture and then dipped in water showed a pH≧8.

After 16 hrs at room temperature under nitrogen, an aliquot of the reaction mixture (3 drops) was diluted in 10 mL 50% aqueous acetonitrile. LC/MS showed the desired product with the M+1 ion at 1087.4 m/z. Starting amine 23 was not detected in the LC-MS trace and 2-3 unknown impurities were detected. The clear light amber solution was added to an addition funnel and kept under nitrogen. This solution was added dropwise to magnetically stirred water (1,400 mL) containing 1M aqueous HCl (30 mL; 30 mmol) over a period of 45 minutes. The pH of the aqueous solution was monitored with a pH electrode and 1M aqueous HCl (28.5 mL; 28.5 mmol) was added periodically to keep the pH between 3 and 3.5. The final pH was 3.1. The resulting cream slurry was suction filtered onto a sintered funnel. The sintered surface of the funnel was occasionally scrapped with a spatula to expedite filtration to give a wet cream solid. The solid was thoroughly washed and mixed with water (200 mL×5) in the funnel without vacuum using a spatula.

After several washings, the rate of filtration was relatively facile and the cake suspended well in the water. The cake was washed as described above with additional water (200 mL×3) in a final effort to remove NMP. The cake was sucked dry on the filter and then transferred as a free flowing, cream solid to an evaporating dish; 25.9 g. The solid was dried in a vacuum oven at 45° C. (11:40 am) for 5 hrs to give a cream solid that was almost dry; 9.75 g. This material was dried without heat overnight.

Amount=9.6 g.≧94% assay with only trace impurities.
Yield=92.9%

STEP 18

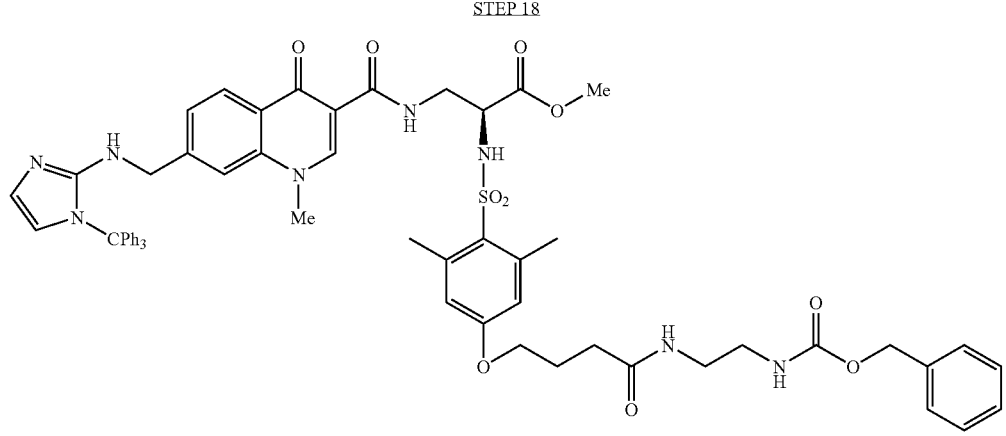

24
$C_{60}H_{62}N_8O_{10}S$
Mol. Wt.: 1087.25

$H_2$ (50 psi), Pd/C
MeOH

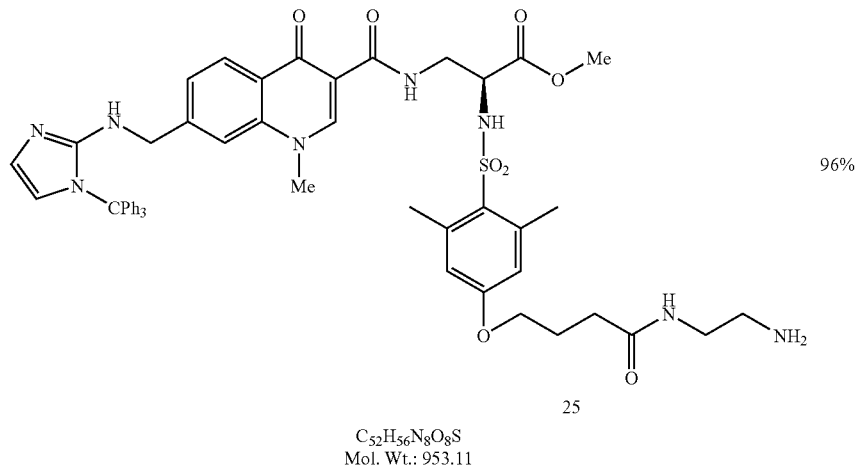

25

$C_{52}H_{56}N_8O_8S$
Mol. Wt.: 953.11

Procedure:

In a 2.5 L Parr bottle, a solution of the N-carbobenzoxy intermediate 24 (9.05 g; 8.3 mmol) in 905 mL methanol containing Degussa E101 NE/W 10% palladium on carbon (2.0 g) was pressurized and depressurized with hydrogen six times to remove residual air on the large Parr shaker. The bottle was pressurized to 44.5 psig with hydrogen and shook on the Parr hydrogenator.

After 20.5 hrs under hydrogen pressure, an aliquot (0.3 mL) was dissolved in 15 mL 33% aqueous acetonitrile and filtered with a Whatman mini-uniprep (0.45μ PFTE filter).

LC/MS analysis showed the desired product with no detectable starting material. The catalyst slurry was suction filtered through a prewetted and packed pad of Celite 545 (41.2 g) topped with a piece of filter paper. The catalyst and Celite pad were washed with methanol (100 mL×3). The light yellow filtrate was concentrated on a rotary evaporator at 35° C. to give a beige solid; 8.2 g. This solid was dried in the vacuum desiccator at room temperature and 0.15 torr overnight.

Amount=7.75 g.≧94% assay by DAD.

Yield=97.3%

STEP 19

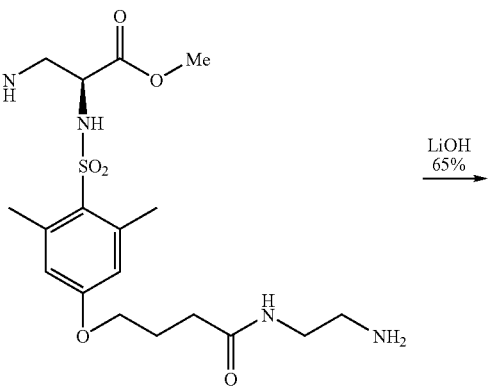

25

$C_{52}H_{56}N_8O_8S$
Mol. Wt.: 953.11

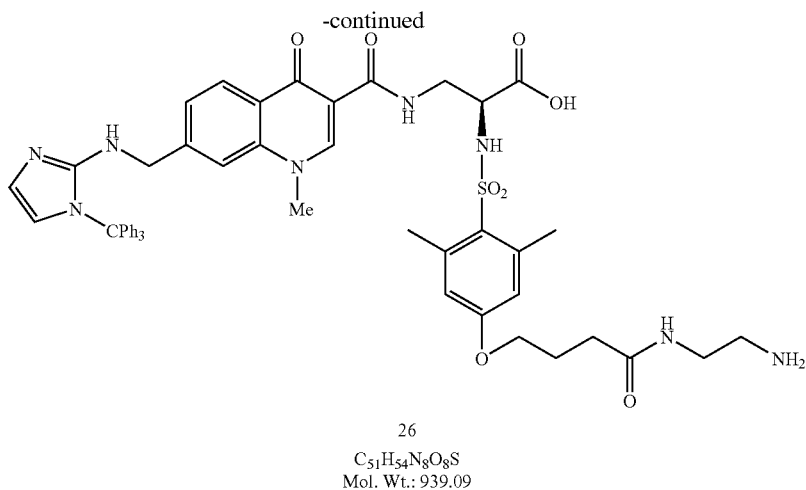

26
C₅₁H₅₄N₈O₈S
Mol. Wt.: 939.09

Procedure:
Compound 25, 210 mg (0.22 mmol) was dissolved in 6 mL of 5:1 (v:v) THF/H₂O. To this solution was added 200 uL of 3N LiOH (aq.) and the resulting two phase system stirred for 3.5 h under Argon at ambient temperature. After 3.5 h the pH of the reaction mixture was adjusted to ca. 6 using 1N HCl (aq.). The THF was removed by purging the reaction mixture with Argon giving a white slurry (Attempt to remove in vacuo caused severe foaming). To this slurry was added 5 mL H₂O and the resulting slurry filtered through a fine glass fritted funnel (slow filtration). The solid was washed with 10 mL H₂O and air dried giving 134 mg (0.14 mmol, 65%) of 26.

STEP 20

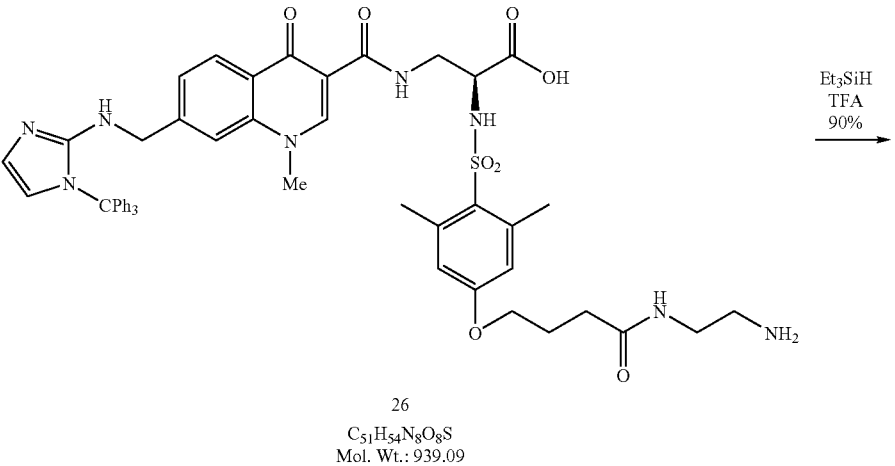

26
C₅₁H₅₄N₈O₈S
Mol. Wt.: 939.09

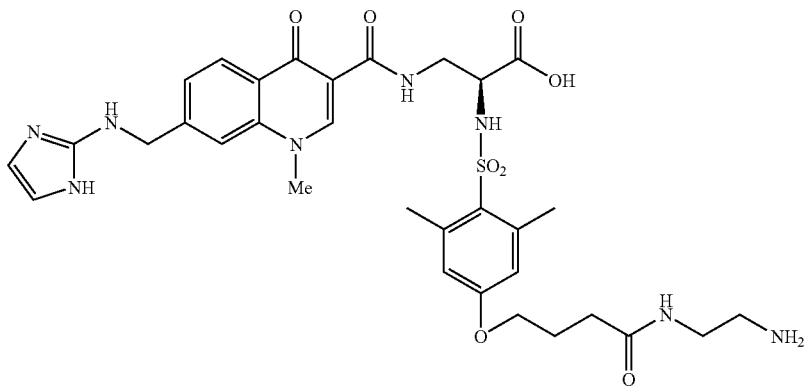

27

Procedure:

Compound 26 (132 mg, 0.14 mmol) was dissolved in 5 mL TFA (Sigma-Aldrich). To this solution was added, under Argon, 0.5 mL of $Et_3SiH$ (Alfa Aesar). The reaction mixture was heated to 70° C. under Argon for 1 hr. The reaction was then allowed to cool to ambient temperature (white solid ppt. from reaction). The crude reaction mixture was filtered through a 0.45 micron syringe filter. To the filtrate was added 25 mL $CH_2Cl_2$ and the resulting solution concentrated in vacuo at 35° C. TO the resulting oil was added a second portion of 25 mL $CH_2Cl_2$ and this solution was concentrated in vacuo at 35° C. To the residue was added 25 mL hexane, warmed to 40° C., with the resulting liquid layer decanted off of the remaining residue. A second portion of 25 mL hexane was added and the above procedure repeated. The remaining residue was dried in vacuo at 40° C. giving 117 mg of 27 (90% based on product as bis-TFA salt).

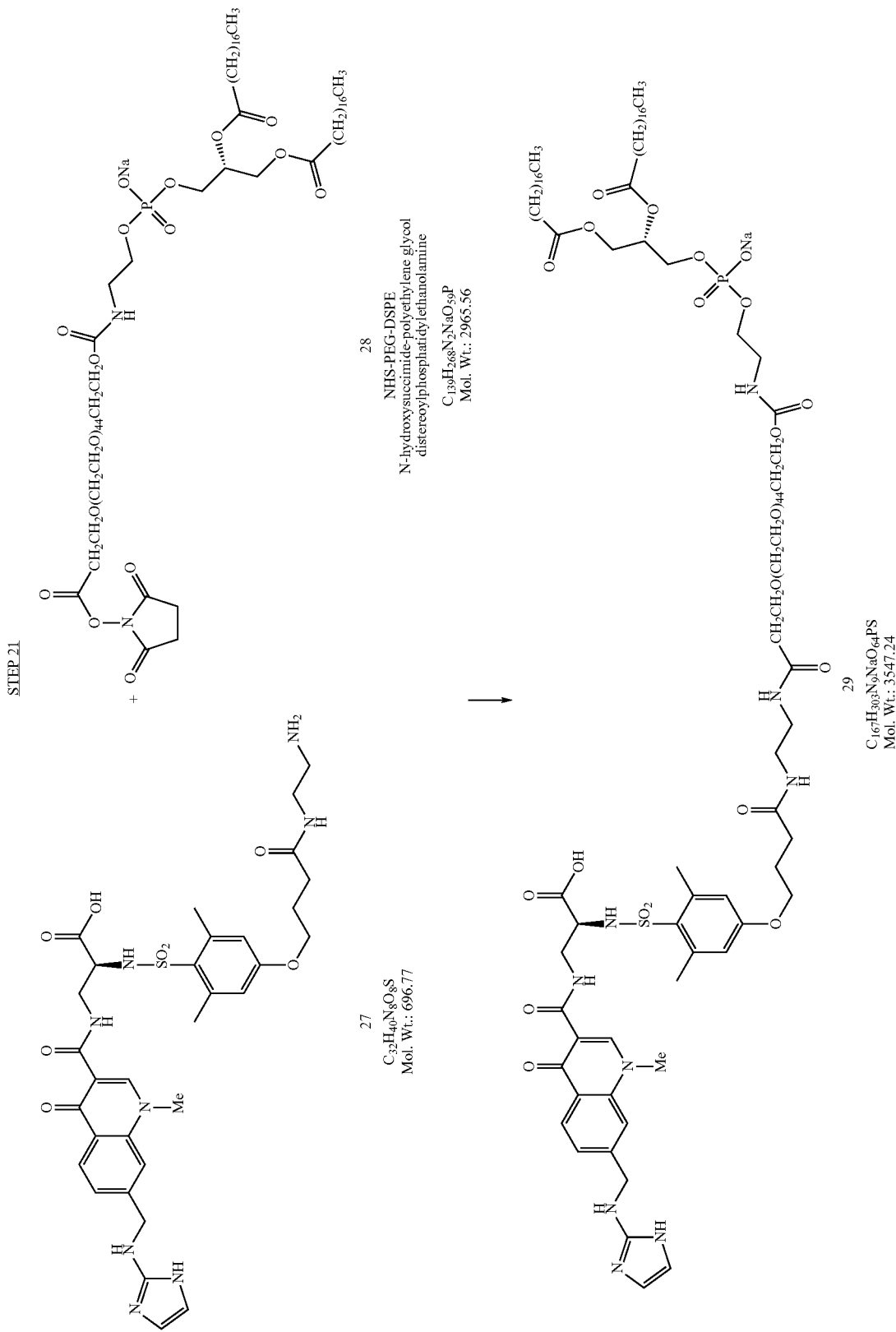

A 100 mL RB flask was charged with 0.508 g of 28 (0.144 mmol based on 84% purity), 142 mg of 27 as the bis-TFA salt (0.154 mmol), 3 mL anhydrous DMF and finally 60 μL of i-Pr$_2$NEt. The homogeneous reaction was stirred at ambient for 48 h. The crude reaction was concentrated in vacuo at 45° C.

The residue was chromatographed on 25 g of silica gel using a step gradient as follows:
1) CHCl$_3$:MeOH 3:1 (v:v)—3 column volumes
2) CHCl$_3$:MeOH:H$_2$O 75:24:1 (v:v:v)—4 column volumen
3) CHCl$_3$:MeOH:H$_2$O 75:23:2 (v:v:v)—4 column volumen
4) CHCl$_3$:MeOH:H$_2$O 75:22:3 (v:v:v)—4 column volumen The desired product is in the fractions collected from the final gradient. Concentration of fractions containing 29 gave a clear glassy solid which was dissolved in 50:50 CH$_3$CN:H$_2$O, diluted with an equal volume of H$_2$O and then lyophilized to a spongy white solid (145.5 mg, 28.5%)

The invention claimed is:

1. A compound of the formula

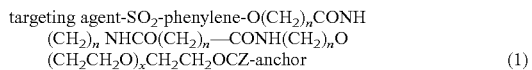

targeting agent-SO$_2$-phenylene-O(CH$_2$)$_n$CONH(CH$_2$)$_n$NHCO(CH$_2$)$_n$—CONH(CH$_2$)$_n$O(CH$_2$CH$_2$O)$_x$CH$_2$CH$_2$OCZ-anchor    (1)

wherein each n is independently 1-4;
x is an integer of 20-60;
Z is =NH or =O;
the targeting agent is a moiety containing an amino group or a hydroxyl group for coupling to the remainder of the molecule; and
the anchor is a lipophilic compound for embedding the compound in a lipid based particulate.

2. The compound of claim 1 wherein the targeting agent targets an integrin.

3. The compound of claim 1 wherein the targeting agent is an antibody or immuno-reactive fragment thereof, or
wherein the targeting agent is a ligand for a receptor.

4. The compound of claim 1 wherein the anchor is the residue of a phosphatidyl lipid.

5. The compound of claim 4 wherein the anchor is a residue of phosphatidyl ethanolamine.

6. The compound of claim 1 wherein x is an integer of 40-50.

7. A lipid-based particulate formulation wherein said lipid-based particles comprise a multiplicity of molecules of the compound of claim 1.

8. The formulation of claim 7 wherein the particles further comprise a therapeutic or diagnostic agent.

9. The particulate formation of claim 8 wherein the therapeutic agent is a drug, and/or
wherein the diagnostic agent is a chelated metal for MRI imaging, or
wherein the therapeutic or diagnostic agent is a radionuclide.

10. The particulate formation of claim 8 wherein the lipid-based particles are liposomes, micelles, or nanoparticles containing cores consisting of liquid fluorocarbon coated with lipid/surfactant.

11. The particulate formation of claim 10 wherein the lipid-based particles are nanoparticles containing cores consisting of liquid fluorocarbon coated with lipid/surfactant.

12. A method to target a desired destination in a subject which comprises administering to said subject the formulation of claim 8.

* * * * *